United States Patent
Neukart et al.

(10) Patent No.: US 12,033,728 B2
(45) Date of Patent: Jul. 9, 2024

(54) SIMULATING ELECTRONIC STRUCTURE WITH QUANTUM ANNEALING DEVICES AND ARTIFICIAL NEURAL NETWORKS

(71) Applicant: VOLKSWAGEN AKTIENGESELLSCHAFT, Wolfsburg (DE)

(72) Inventors: Florian Neukart, San Francisco, CA (US); Michael Streif, San Francisco, CA (US); David Von Dollen, San Francisco, CA (US); Tanja Graf, Braunschweig (DE); Thomas Schladt, Braunschweig (DE); Arne-Christian Voigt, Wolfsburg (DE); Jonathan Edward Mueller, Wolfsburg (DE)

(73) Assignee: VOLKSWAGEN AKTIENGESELLSCHAFT, Wolfsburg (DE)

( * ) Notice: Subject to any disclaimer, the term of this patent is extended or adjusted under 35 U.S.C. 154(b) by 0 days.

(21) Appl. No.: 18/212,646

(22) Filed: Jun. 21, 2023

(65) Prior Publication Data
US 2024/0071576 A1    Feb. 29, 2024

Related U.S. Application Data

(63) Continuation of application No. 16/810,483, filed on Mar. 5, 2020, now Pat. No. 11,776,666.
(Continued)

(51) Int. Cl.
*G06G 7/48* (2006.01)
*G06F 30/20* (2020.01)
(Continued)

(52) U.S. Cl.
CPC ............ *G16C 20/30* (2019.02); *G06F 30/20* (2020.01); *G06N 3/04* (2013.01); *G06N 3/08* (2013.01); *G06N 10/00* (2019.01); *G16C 20/70* (2019.02)

(58) Field of Classification Search
USPC ....................... 703/1, 4, 11, 12, 13, 14, 15
See application file for complete search history.

(56) References Cited

U.S. PATENT DOCUMENTS

| | | | | |
|---|---|---|---|---|
| 10,325,218 B1* | 6/2019 | Zeng | ...................... | G06N 20/00 |
| 10,885,678 B2* | 1/2021 | Bishop | .................. | G06N 10/00 |

(Continued)

FOREIGN PATENT DOCUMENTS

CN    104715096 A    6/2015

OTHER PUBLICATIONS

United States Patent and Trademark Office, U.S. Appl. No. 16/810,483, Final Office Action dated Nov. 3, 2022.
(Continued)

*Primary Examiner* — Brian Ngo
(74) *Attorney, Agent, or Firm* — Shield Intellectual Property PC; Zhichong Gu

(57) ABSTRACT

Approaches, techniques, and mechanisms are disclosed for predicting molecular electronic structural information. According to one embodiment, quantum simulation results are generated for a molecule based on a quantum simulation of an electronic structure of the molecule. The quantum simulation of the electronic structure of the molecule is performed with quantum processing units. An input vector comprising data field values derived from the quantum simulation results for the molecule is created. An electronic structural information prediction model is applied to generate, based at least in part on the input vector, predicted electronic structural information for the molecule.

21 Claims, 9 Drawing Sheets

Related U.S. Application Data

(60) Provisional application No. 62/814,904, filed on Mar. 7, 2019.

(51) Int. Cl.
  *G06N 3/04* (2023.01)
  *G06N 3/08* (2023.01)
  *G06N 10/00* (2022.01)
  *G16C 20/30* (2019.01)
  *G16C 20/70* (2019.01)

(56) References Cited

U.S. PATENT DOCUMENTS

2020/0058376 A1\* 2/2020 Dean ..................... G16B 40/00
2020/0286595 A1 9/2020 Neukart et al.

OTHER PUBLICATIONS

United States Patent and Trademark Office, U.S. Appl. No. 16/810,483, Non-Final Office Action dated Jul. 7, 2022.
United States Patent and Trademark Office, U.S. Appl. No. 16/810,483, Non-Final Office Action dated Feb. 16, 2023.
United States Patent and Trademark Office, U.S. Appl. No. 16/810,483, Notice of Allowance dated Jun. 7, 2023.

\* cited by examiner

FIG. 3C

| bond_lengths | hydrogen | lithium | oxygen | beryllium | phosphorus | nitrogen | cpu_energies |
|---|---|---|---|---|---|---|---|
| 0 | 0.3 | 1 | 1 | 0 | 0 | 0 | 0 | -5.863586 |
| 1 | 0.4 | 1 | 1 | 0 | 0 | 0 | 0 | -6.610879 |
| 2 | 0.5 | 1 | 1 | 0 | 0 | 0 | 0 | -7.028410 |
| 3 | 0.6 | 1 | 1 | 0 | 0 | 0 | 0 | -7.299541 |
| 4 | 0.7 | 1 | 1 | 0 | 0 | 0 | 0 | -7.465945 |
| 5 | 0.8 | 1 | 1 | 0 | 0 | 0 | 0 | -7.615770 |

FIG. 3D

| | bond_lengths | hydrogen | lithium | oxygen | beryllium | phosphorus | nitrogen | cpu_energies |
|---|---|---|---|---|---|---|---|---|
| 143 | 1.1 | 2 | 1 | 1 | 0 | 0 | 0 | -62.807113 |
| 144 | 1.2 | 2 | 1 | 1 | 0 | 0 | 0 | -63.180701 |
| 145 | 1.3 | 2 | 1 | 1 | 0 | 0 | 0 | -63.505637 |
| 146 | 1.4 | 2 | 1 | 1 | 0 | 0 | 0 | -63.788450 |
| 147 | 1.5 | 2 | 1 | 1 | 0 | 0 | 0 | -64.047552 |

450 generate quantum simulation results for a molecule 452 create an input vector comprising data field values deriving from the quantum simulation results for the molecule 454 apply an electronic structural information prediction model to generate predicted electronic structural information for the molecule 466

*FIG. 4B*

SIMULATING ELECTRONIC STRUCTURE WITH QUANTUM ANNEALING DEVICES AND ARTIFICIAL NEURAL NETWORKS

CROSS-REFERENCE TO RELATED APPLICATIONS

This application is a continuation of U.S. patent application Ser. No. 16/810,483 filed on Mar. 5, 2020, which claims priority to U.S. Provisional Patent Application No. 62/814,904 filed on Mar. 7, 2019, the contents of all of which are incorporated herein by reference in their entireties. The applicant(s) hereby rescind any disclaimer of claim scope in the parent application(s) or the prosecution history thereof and advise the USPTO that the claims in this application may be broader than any claim in the parent application(s).

TECHNICAL FIELD

Embodiments relate generally to simulating electronic structure, and, more specifically, to techniques for simulating electronic structure with quantum annealing devices and artificial neural networks.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

In principle, the electronic structure of a molecule, along with numerous properties derived from the electronic structure, can be determined exactly by solving the Schrödinger equation. However, for all but the simplest systems, an analytical solution to the Schrödinger equation is not available. Nevertheless, numerical methods have been developed to enable classical computers (nonquantum) to reach approximate solutions. These approaches, including but limited to Hartree-Fock methods, quantum Monte Carlo methods, density functional theory (DFT) or configuration interaction methods (CI), exhibit varying degrees of accuracy that are typically inversely related to their computational cost. This trade-off between accuracy and computational cost, further compounded with typically poor scaling of these methods, makes their application to molecular systems, where size and accuracy are both important, unfeasible.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3C and FIG. 3D illustrate an atom-specific input vector (or instances thereof) for an artificial neural network based predictor;

FIG. 4A and FIG. 4B illustrates example flows 400 and 450 for predicting energies for molecules.

DETAILED DESCRIPTION

Figure 1:
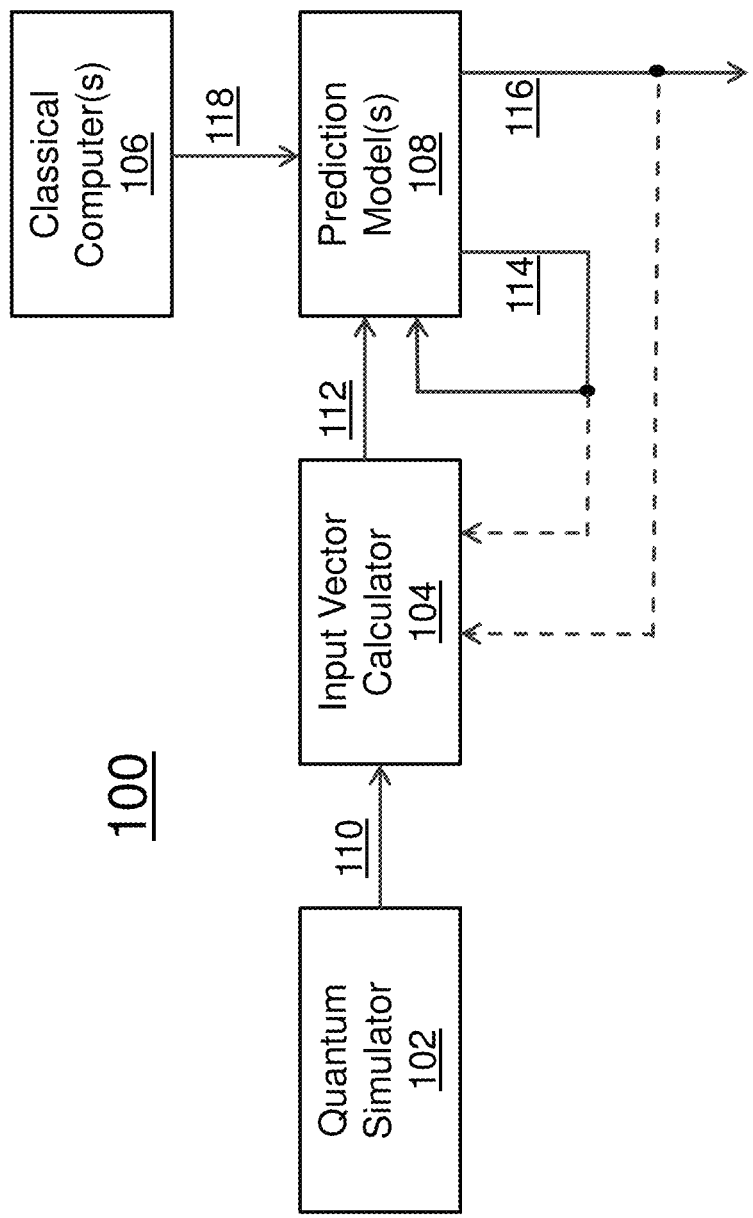
FIG. 1 is an illustrative view of various aspects of an example system in which the techniques described herein may be practiced.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein according to the following outline:
  1.0. General Overview
  2.0. Structural Overview
    2.1. Quantum Simulator
    2.2. Input Vector Calculator
    2.3. Classical Computation
    2.4. Prediction Models
    2.5. Miscellaneous
  3.0. Functional Overview
    3.1. Formulations of Hamiltonian for Molecules
    3.2. Optmization Problem Formulation for Quantum Simulation
    3.3. Quantum Simulation
    3.4. Training and Applying Prediction Models
    3.5. Application Phase
  4.0. Example Process Flows
  5.0. Implementation Mechanism—Hardware Overview
  6.0. Extensions and Alternatives

1.0. GENERAL OVERVIEW

Techniques as described herein can be used to implement a hybrid algorithm for electronic structure simulation. The hybrid algorithm combines quantum-quantum simulation of molecular electronic structure with classical (non-quantum) machine learning for the purpose of obtaining information. As used herein, quantum-quantum simulation or simply quantum simulation refers to using one or more quantum processing units (QPUs) to perform quantum computing (e.g., quantum annealing, etc.) that simulates the electronic structure of a system or molecule based on a specific quantum formulation (or quantum representation) of the system or molecule. Quantum simulation as described herein may include but is not necessarily limited to only energy calculation. Classical (non-quantum) machine learning as described herein refers to using one or more (e.g., non-quantum, etc.) computing devices to perform machine learning that narrows or minimizes prediction differences between the hybrid algorithm and other classical computational approaches of quantum systems or molecules. Example classical computational approaches of quantum systems or molecules may include, but are not necessarily limited to only, any of: Hartree-Fock methods, quantum Monte Carlo methods, density functional theory or configuration interaction methods, etc. Example classical machine learning includes but is not necessarily limited to only artificial neural networks (ANNs).

In some operational scenarios, one or more quantum annealing systems can be used to simulate molecular electronic structure of molecules. Such quantum simulation may be applied to some molecules such as LiH or BeO for which full configuration interaction (FCI) energies from classical computational approaches of quantum systems or molecules are available, as well as to some other molecules for which FCI energies from classical computational approaches are not available.

Under techniques as described herein, differences between predicted energies obtained through quantum simulation and FCI energies can be corrected with ANNs. The ANNs can be first trained with training data that comprises energies obtained through quantum simulation and FCI energies for some molecules. These molecules included in the training data may be simple enough for the classical computational approaches to obtain the FCI energies with available computing resources.

The ANNs used for machine learning can use the (simulation) energies in the training data obtained through quantum simulation as input to generate predicted FCI energies (also denoted as "FCI predictions"). Operational parameters for the ANNs may be optimized to improve prediction accuracy through minimizing errors or differences (e.g., via back propagation, etc.) between the predicted FCI energies and the (real) FCI energies in the training data obtained through the classical computational approaches.

Once trained, the ANNs with the optimized operational parameters can use (simulation) energies obtained through quantum simulation for molecules—which may not be a part of the training data—over different bond lengths as input to generate predicted FCI energies for these molecules for which (real) FCI energies may not be available from the classical computational approaches.

This approach allows a hybrid system as described herein to combine both quantum simulation and classical machine learning and to determine FCI energies faster than a purely classical approach (e.g., Hartree-Fock methods, quantum Monte Carlo methods, density functional theory or configuration interaction methods, etc.). Additionally, optionally or alternatively, this approach allows the hybrid system to scale quantum computing devices relatively easily and to generate FCI predictions for molecules that may not be possible to be calculated purely classically.

Electronic structural information generated under techniques as described herein can be used to search for materials of suitable properties, including but not limited to battery materials and high temperature materials, in a variety of industries and/or real-world applications.

Approaches, techniques, and mechanisms are disclosed for predicting molecular electronic structural information. According to one embodiment, quantum simulation results are generated for a molecule based on quantum simulation of electronic structure of the molecule. The quantum simulation of electronic structure of the molecule is performed with one or more quantum processing units. An input vector comprising data field values deriving from the quantum simulation results for the molecule as generated by the quantum simulation of electronic structure of the molecule is created. An electronic structural information prediction model is applied to generate, based at least in part on the input vector, predicted electronic structural information for the molecule.

In other aspects, the invention encompasses computer apparatuses and computer-readable media configured to carry out the foregoing techniques.

2.0. STRUCTURAL OVERVIEW

FIG. 1 is an illustrative view of various aspects of an example system 100 in which the techniques described herein may be practiced, according to an embodiment. System 100 comprises one or more computing devices. The one or more computing devices comprise any combination of hardware and software configured to implement the various logical components described herein, including components such as quantum simulator system 102, input vector calculator 104, prediction model(s) 108, and classical computer 106. For example, the one or more computing devices may include one or more memories storing instructions for implementing the various components described herein, one or more hardware processors configured to execute the instructions stored in the one or more memories, and various data repositories in the one or more memories for storing data structures utilized and manipulated by the various components.

2.1. Quantum Simulator

System 100 comprises a quantum simulator 102 that operates with one or more QPUs to simulate electronic structure of molecules and generating quantum simulation results 110 for the molecules. Example quantum simulators or QPUs with which quantum simulators operate may include, but are not limited to only, any of: quantum annealing systems, D-Wave systems, quantum systems with relatively shallow circuits, quantum systems with relatively low requirements on coherency times, etc.

Quantum simulation of electronic structures as described herein may be performed for a relatively large set of molecules, which may include simple molecules, complex molecules, small molecules, large molecules, di-atomic molecules, tri-atomic molecules, and so forth. In some operational scenarios, quantum simulation results 110 as obtained through quantum simulation of electronic structures of molecules may comprise respective quantum simulation energies (also denoted as "QPU energies") for the molecules whose electronic structures are simulated by quantum simulator 102.

The quantum simulation results 110 as generated from the quantum simulator 102 or the QPUs with the quantum simulator 102 operates can be provided by quantum simulator 102 to other components or devices in system 100.

2.2. Input Vector Calculator

System 100 comprises an input vector calculator 104 that receives quantum simulation results 110 as input and calculates or derives input vectors 112 from some or all of the quantum simulation results 110.

The input vectors 112 comprise data field values (or features) calculated or derived from the quantum simulation results 110 in the training data. These data field values in the input vectors may include, but are not necessarily limited to only, quantum simulation energies, operational parameters used in quantum simulation, etc.

Additionally, optionally or alternatively, in operational scenarios in which multiple prediction models are deployed, input vectors used by a later executed prediction model (e.g., later executed ANNs, etc.) may incorporate information or data field values derived from prediction results of an earlier executed prediction model (e.g., earlier executed ANN(s), etc.).

The input vectors 112 can be directly or indirectly fed, for example by input vector calculator 104, as input into one or more prediction models 108.

2.3. Classical Computation

System 100 further comprises one or more classical computers 106 that operates with one or more (non-quantum) computing processors to perform classical computations (e.g., Hartree-Fock methods, quantum Monte Carlo methods, density functional theory or configuration interaction methods, etc.) to derive classically determined results 118 that include classically computed molecular electronic structural information. Example classical computers or (non-quantum) computing processors with which quantum simulators operate may include, but are not limited to only, any of: computer servers, desktop computers, personal computers, computer clusters, mainframe computers, parallel computers, supercomputers, etc.

Classic computation of molecular electronic structural information as described herein may be computationally intensive, and hence may be performed for only a relatively small subset of molecules that represents a relatively small, proper subset among all molecules in the relatively large set of molecules (whose electronic structures are simulated by quantum simulator 102) as mentioned above. The subset of molecules may include relatively simple molecules, relatively small molecules, di-atomic molecules, etc. In some operational scenarios, the classically determined results 118 as obtained through classical computations performed by classical computers 106 may comprise respective FCI energies for molecules in the subset of molecules. As used herein, (classically computed) FCI energies in the classically determined results 118 may also be referred to as "real FCI energies."

Some or all of the classically determined results 118 as generated by classical computers 106 or (non-quantum) computing processors with which classical computers 106 operate can be directly or indirectly fed, for example by classical computers 106, as input into prediction models 108.

2.4. Prediction Models

Prediction models 108 may be implemented in system 100 for predicting or generating molecular electronic structural information. Example molecular electronic structural information predicted or generated by prediction models 108 may include, but is not necessarily limited to only, (predicted) FCI energies. In some operational scenarios, some or all of prediction models 108 used to predict molecular electronic structural information or FCI energies may be implemented as ANNs.

In some operational scenarios, since both (classically computed) FCI energies and quantum simulation results 110 including quantum simulation energies are available for the relatively small subset of molecules, training data may be generated to comprise input vectors 112 calculated or derived from the quantum simulation results 110 and real FCI energies (or ground truths) derived from classically determined results for the relatively small subset of molecules. The training data for the prediction model may comprise a set of training data instances. Each training data instance in the set of training data instances may correspond to a respective molecule in the relatively small subset of molecules and comprise instance-specific ground truth represented by FCI energies computed for the respective molecule and instance-specific input vector for the respective molecule.

In a model training phase, a prediction model 108 as described herein may be first trained or optimized to predict FCI energies from the input vectors in the training data. Operational parameters (and even configurations) of the prediction model may be (e.g., repeatedly, iteratively, recursively, etc.) adjusted or improved to minimize errors or differences between predicted FCI energies as generated by the prediction model for each molecule represented in the training data and real FCI energies in the training data for the molecule.

In a (non-training) model application phase, quantum simulation is performed for (to-be-predicted) molecules that may or may not be represented in the training data. For example, quantum simulator 102 may generate quantum simulation results 110 by performing quantum simulation of molecular electronic structures for the (to-be-predicted) molecules—at least some of which may be in the relatively large set of molecules but not in the relatively small subset of molecules—that FCI energies from classically determined results are not available.

Input vector calculator 104 receives the quantum simulation results for the (to-be-predicted) molecules as generated by quantum simulator 102 and calculates or derives corresponding input vectors for the (to-be-predicted) molecules from the quantum simulation results.

Prediction models 108—operating with the optimized operational parameters and operational configuration—receive the input vectors for the (to-be-predicted) molecules as calculated or derived by input vector calculator 104 and use the input vectors for the (to-be-predicted) molecules to generate predicted FCI energies for the (to-be-predicted) molecules, regardless of whether FCI energies from classical computation are available or not for the (to-be-predicted) molecules.

2.5. Miscellaneous

System 100 illustrates only one of many possible arrangements of components configured to provide the functionality described herein. Other arrangements may include fewer, additional, or different components, and the division of work between the components may vary depending on the arrangement. For instance, classical computation techniques as described herein may be practiced in other types of systems that are not necessarily classical computers to generate classically determined results for molecular electronic structural information. In some operational scenarios, quantum computing devices other than quantum simulator as described herein may be used to generate FCI energies to be used for comparison with predicted FCI energies generated from quantum simulation results.

3.0. FUNCTIONAL OVERVIEW

In an embodiment, some or all techniques and/or methods described below may be implemented using one or more computer programs, other software elements, and/or digital logic in any of a general-purpose computer or a special-purpose computer, while performing data retrieval, transformation, and storage operations that involve interacting with and transforming the physical state of memory of the computer.

3.1. Formulations of Hamiltonian for Molecules

Classical computation of molecular electronic structure information may be feasible for only a few small simple di-atomic molecules and may not be feasible for other molecules. To overcome this limitation or hurdle, quantum simulators—quantum systems which simulate other quantum systems—may be used to derive molecular electronic structural information that approximates what could be theoretically computed.

Due to emerging technical possibilities, recent research has focused on developing approaches to solve electronic structure problems by the use of quantum computers, in particular gate model devices. Some quantum algorithms (e.g., the Variational Quantum Eigensolver (VQE), the Phase Estimation Algorithm (PEA), etc.) utilize the possibility of representing atomic orbitals as qubits of the quantum chip, and so are in theory able to simulate the quantum system to find the ground state of small molecules. However, current gate model devices suffer from various serious challenges in terms of availability of a small number of qubits, frequent errors caused by imperfect gates and qubits, and decoherence effects (e.g., only a few milliseconds available for maintaining quantum coherence, insufficient time to squeeze sufficient quantum computation necessary for a quantum computation, etc.). These challenges all limit the time of a single quantum computation and hence limit the number of usable gates and the complexity of usable quantum circuits. Accordingly, research may focus on finding hardware-efficient simulations or shallow circuits for solving or avoiding these kinds of problems or challenges.

Under techniques as described herein, quantum simulation may be performed to simulate electronic structures of molecules. By way of illustration but not limitation, a Hamiltonian for a system (e.g., a to-be-simulated molecule, a to-be-predicted molecule, etc.) consisting of M nuclei and N electrons may be written in atomic units as follows:

$$H = -\sum_{i=1}^{N} \frac{1}{2}\nabla_i^2 - \sum_{A=1}^{M} \nabla_A^2 - \sum_{i=1}^{N}\sum_{A=1}^{M} \frac{Z_A}{R_{iA}} + \sum_{i=1}^{N}\sum_{j>i}^{N} \frac{1}{r_{ij}} + \sum_{A=1}^{M}\sum_{B>A}^{M} \frac{Z_A Z_B}{R_{AB}} \quad (1)$$

where H is the Hamiltonian for a system containing N electrons and M nuclei with $r_i$ and $R_A$ as respective position vectors. $M_A$ represents the ratio of nucleus A's mass to the mass of an electron. $Z_A$ (or $Z_B$) represents the atomic number of nucleus A (or nucleus B). $\nabla_i^2$ and $\nabla_A^2$ represent respective Laplacian operators involving differentiation with respect to the coordinates of the i-th electron and the A-th nucleus. $R_{iA}$ represents the distance between the i-th electron and the A-th nucleus. $R_{AB}$ represents the distance between the A-th nucleus and the B-th nucleus.

The terms of expression (1) respectively describe the following quantities of the system (e.g., the to-be-simulated molecule, the to-be-predicted molecule, etc.): (a) operator for kinetic energy of electrons; (b) operator for kinetic energy of nuclei; (c) Coulomb attraction between electrons and nuclei; (d) repulsion between electrons; and (e) repulsion between nuclei.

The notation in expression (1) is well known as first-quantized formulation of electronic structure problems and was subject of research itself. Nevertheless, recent research has focused on using second quantized formulations for doing quantum computations. Under the second quantized formulation, expression (1) may be (alternatively) written as follows:

$$H = \sum_{i,j} h_{ij} a_i^\dagger a_j + \frac{1}{2}\sum_{i,j,k,l} h_{ijkl} a_i^\dagger a_j^\dagger a_k a_l \quad (2)$$

where $a_i^\dagger$ and $a_j$ are the fermionic creation and annihilation operators for a specific fermionic mode i and j with $\{a_i^\dagger, a_j\} = \delta_{ij}$. The parameters $h_{ij}$ and $h_{ijkl}$ are the one- and two-particle integrals for a specific, problem-dependent basis set $|\Psi\rangle$, which have been chosen $$h_{ij} = \langle\psi_i|\left(-\frac{\nabla_i^2}{2} - \sum_A \frac{Z_A}{|r_i - R_A|}\right)|\psi_j\rangle \quad (3)$$

$$h_{ijkl} = \langle\psi_i\psi_j|\frac{1}{|r_i - r_j|}|\psi_k\psi_l\rangle$$

where $Z_A$ is the atomic number of the nucleus, $|r_i-R_A|$ is the distance between the ith electron and the Ath nucleus, $|r_i-r_j|$ is the distance between the ith and the jth electron, and $\nabla_i^2$ is the Laplacian operator involving differentiation with respect to the coordinates of the ith electron.

As quantum computing devices utilize qubits, the Hamiltonian in the second quantization formulation of fermions in expression (2) may be converted to a qubit representation, for example by using Jordan-Wigner or Bravyi-Kitaev transformation, which leads in general to a Hamiltonian of the following form:

$$H = \sum_{i,\alpha} h_\alpha^i \sigma_\alpha^i + \sum_{i,j,\alpha,\beta} h_{\alpha\beta}^{ij}\sigma_\alpha^i\sigma_\beta^j + \sum_{ijk\alpha\beta\gamma} h_{\alpha\beta\gamma}^{ijk}\sigma_\alpha^i\sigma_\beta^j\sigma_\gamma^k + \dots \quad (4)$$

where i represents an index for a (e.g., the i-th, etc.) spin orbital; $\alpha$ (or $\beta$ or $\gamma$) represents any of indices x, y, z for the Pauli matrixes (e.g., $\sigma_\alpha^i$, $\sigma_\beta^j$, $\sigma_\gamma^k$, etc.).

3.2. Optmization Problem Formulation for Quantum Simulation

By way of illustration but not limitation, quantum simulation of electronic structure of a system such as a molecule may be carried out with one or more QPUs that implements quantum annealing to find (e.g., the lowest, the minimum, the global minimum, the local minimum etc.) energy levels or energy level distributions associated with the system.

Quantum annealing belongs to a class of meta-heuristic algorithms suitable for solving optimization problems and sampling tasks. The QPUs may be designed to solve a classical Ising model with a Hamiltonian of the following form:

$$H = \sum_i h_i \sigma_z^i + \sum_{ij} J_{ij}\sigma_z^i\sigma_z^j \quad (5)$$

where each qubit represents a variable, and couplers between qubits represent the costs associated with qubit pairs.

Solving the classical Ising model with a Hamiltonian of the above form is equivalent to solving quadratic unconstrained binary optimization (QUBO) problems. More specifically, the QPUs may be used as a physical implementation of an undirected graph with qubits as vertices and couplers as edges between the qubits (e.g., forming qubit pairs, etc.). A functional form (or an objective function) for the QUBO problem that the QPU is designed to minimize or optimize may be defined or specified as follows:

$$\text{Obj}(x,Q) = x^T \cdot Q \cdot x \quad (6)$$

where x represents a vector of binary variables (e.g., such as qubits, qubits with biases, etc.) of size N, and Q represents an N×N real-valued matrix describing relationships (e.g., couplers, etc.) between the binary variables.

Given the matrix Q, finding binary variable assignments (e.g., states, values, Boolean values, etc.) that minimize the objective function in expression (6) above is equivalent to minimizing an Ising model, which is a known NP-hard problem in classical computing. A scalable solution for solving such problem by classical computers may be difficult or impossible to find as the dimension or size of the problem increases.

Techniques as described herein may be implemented to simulate an electronic structure problem on a quantum annealing machine operating with QPUs. The quantum simulation may be based on a formulation of the problem in the form of the classical Ising Hamiltonian such as represented in expression (5) above.

In comparison to the general qubit Hamiltonian of such an problem (e.g., in expression (4) above, etc.), which comprises all the Pauli matrixes (e.g., a $\sigma_x$, $\sigma_y$, $\sigma_z$, etc.) as well as k-local terms, the classical Ising formulation (e.g., as represented in expression (5) above, etc.) comprises a specific type (e.g., $\sigma_z$, etc.) of the Pauli matrixes and 2-local terms only.

The general qubit Hamiltonian (e.g., in expression (4) above, etc.) comprising n qubits and all the Pauli matrixes (e.g., $\sigma_x$, $\sigma_y$, $\sigma_z$, etc.) may be mapped to a classical Ising formulation (e.g., as represented in expression (5) above, etc.) comprising rn-qubit and the specific type (e.g., $\sigma_z$, etc.) of the Pauli matrixes using a set of mappings as follows:

$$\sigma_x^i \to \frac{1 - \sigma_z^{ij}\sigma_z^{ik}}{2} S'(j)S'(k)$$

$$\sigma_y^i \to i\frac{\sigma_z^{ik} - \sigma_z^{ij}}{2} S'(j)S'(k)$$

$$\sigma_z^i \to i\frac{\sigma_z^{ij} - \sigma_z^{ik}}{2} S'(j)S'(k)$$

$$I^i \to \frac{1 + \sigma_z^{ij}\sigma_z^{ik}}{2} S'(j)S'(k) \quad (7)$$

where i represents an index in (original) n qubits (in the wave function associated with the pre-converted or original Hamiltonian); j represents an index in r copies of each qubit in the (original) n qubits; S'(j) and S'(k) represent the sign of the j-th or k-th copies of the (original) n qubits in new state(s) of rn qubits. In these mappings, $\sigma_{a=x,y,z}^{ij}$ denote the Pauli matrices acting on the j-th ancillary qubit of the i-th original qubit.

As shown, all the Pauli matrixes (e.g., $\sigma_x$, $\sigma_y$, $\sigma_z$, etc.) on the left-hand-sides (LHSs) of expression (7) are respectively mapped to the specific type (e.g., $\sigma_z$, etc.) of the Pauli matrixes on the right-hand-sides (RHSs). The set of mappings causes the (original) n qubits in the pre-converted or original Hamiltonian to be represented in a mapping space comprising r copies of the n qubits with which the converted Hamiltonian is represented.

Since the general Hamiltonian formulation utilizing orbital spins—as represented in expression (4) above—comprises k-local terms describing k-body interactions, these k-local terms may be further reduced to a 2-local spin Hamiltonian according to the classical Ising model in expression (4), for example by introducing ancillary qubits as follows:

$$\min(\pm x_1 x_2 x_3) = \min(\pm x_4 x_3 + x_1 x_2 - 2x_1 x_4 + 3x_4) \quad (8)$$

The mappings and reductions as indicated in expressions (7) and (8) above cause the general Hamiltonian formulation as represented in expression (4) above to be converted to a classical Ising model Hamiltonian formulation as represented in expression (5) above, as follows $$H = \sum_i h'_i \sigma_z^i + \sum_{i,j} J_{ij} \sigma_z^i \sigma_z^j \quad (9)$$

3.3. Quantum Simulation

Figure 2A:
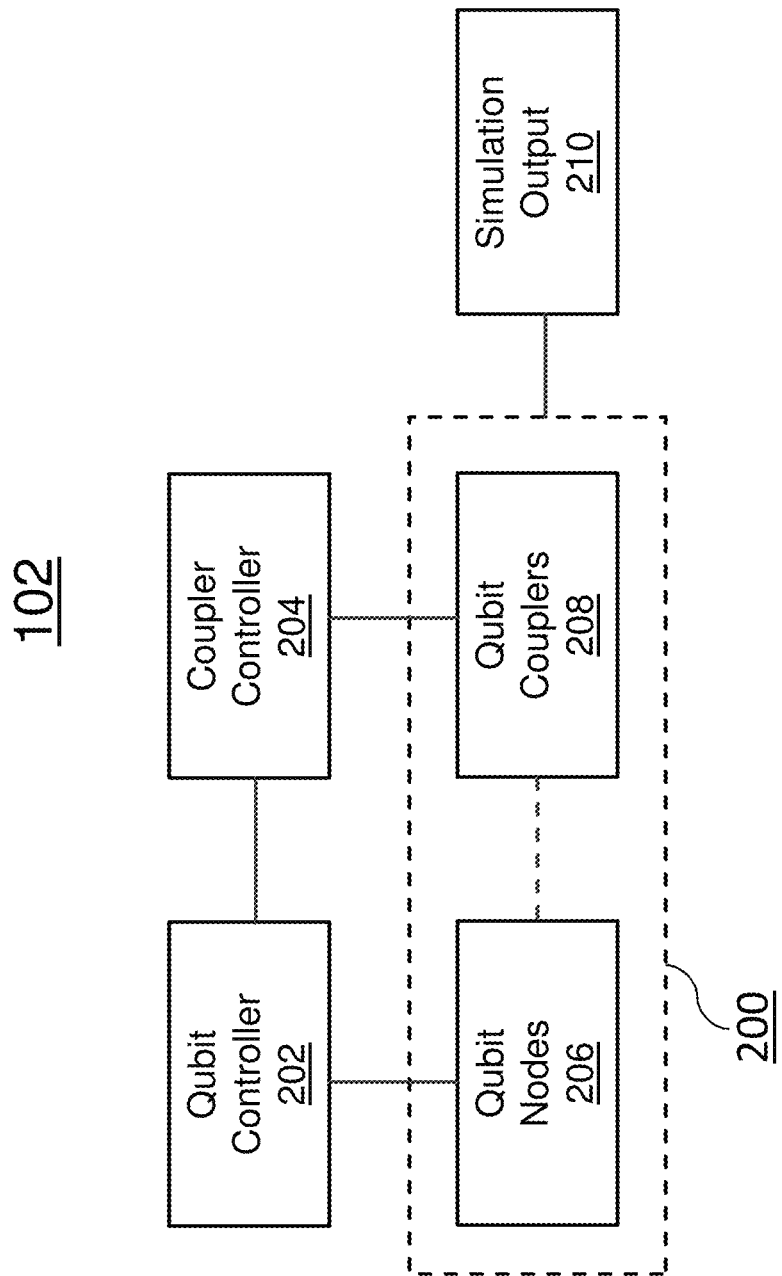
FIG. 2A illustrates an example block diagram for a quantum simulator.

FIG. 2A illustrates an example block diagram for a quantum simulator (e.g., 102 of FIG. 1, etc.), according to one embodiment. The quantum simulator as illustrated in FIG. 2A may be implemented with one or more computing devices and one or more QPUs. The quantum simulator comprises any combination of hardware and software configured to implement the various logical components described herein, including components such as a qubit controller 202, a coupler controller 204, a QPU 200 and a simulation output device 210.

The quantum simulator may include computer processors having one or more memories storing instructions for implementing some or all the components described herein, one or more hardware processors configured to execute the instructions stored in the one or more memories, and various data repositories in the one or more memories for storing data structures utilized and manipulated by the components.

In an embodiment, operations performed in some or all the blocks described below may be implemented using one or more computer programs, other software elements, and/or digital logic in any of a general-purpose computer or a special-purpose computer, while performing data retrieval, transformation, and storage operations that involve interacting with and transforming the physical state of memory of the computer. FIG. 2A illustrates but one example block diagram for a quantum simulator. Other block diagrams and/or configurations may involve additional or fewer blocks, in potentially varying arrangements.

In some operational scenarios, QPU 200 may be implemented as a quantum annealing system (e.g., a D-Wave quantum annealing system, a non D-Wave quantum annealing system, etc.) comprising qubit nodes 206 and qubit couplers 208. The qubit nodes 206 and the qubit couplers 208 may be set up with qubit controller 202 and coupler controller 204 based at least in part on a Hamiltonian formulation of a (quantum) system such as a molecule to simulate an electronic structure of the (quantum) system or the molecule. Combinations of states of the qubit nodes 206 in QPU 200 may be used to collectively represent various quantum states of the (quantum) system or the molecule. Interactions or coupling between the qubit nodes 206 (or any qubit pair therein) may be set up by coupler controller 204 in accordance with coupling terms of the Hamiltonian formulation (e.g., represented in or converted into a mapping space in conformance with the classical Ising model, etc.).

One or more quantum annealing processes may be carried out with the qubit nodes 206 and the qubit couplers 208. A respective portion of quantum simulation results may be obtained or measured by quantum simulator 102 (or simulation output device 210) therein after the completion of each of the quantum annealing processes. The quantum simulation result after the quantum annealing processes may comprise some or all of: (e.g., the lowest, the local minimum, the global minimum, etc.) energy levels, (e.g., probabilistic, probabilistic density, etc.) distributions of energy levels, operational parameters in quantum simulation, operational configurations in quantum simulation, molecular properties, atomic properties, etc. Some or all these results may be outputted by the quantum simulator 102 (or simulation output device 210) to other components of an overall electronic structural information prediction system such as 100 of FIG. 1.

3.4. Training and Applying Prediction Models

Figure 3A:
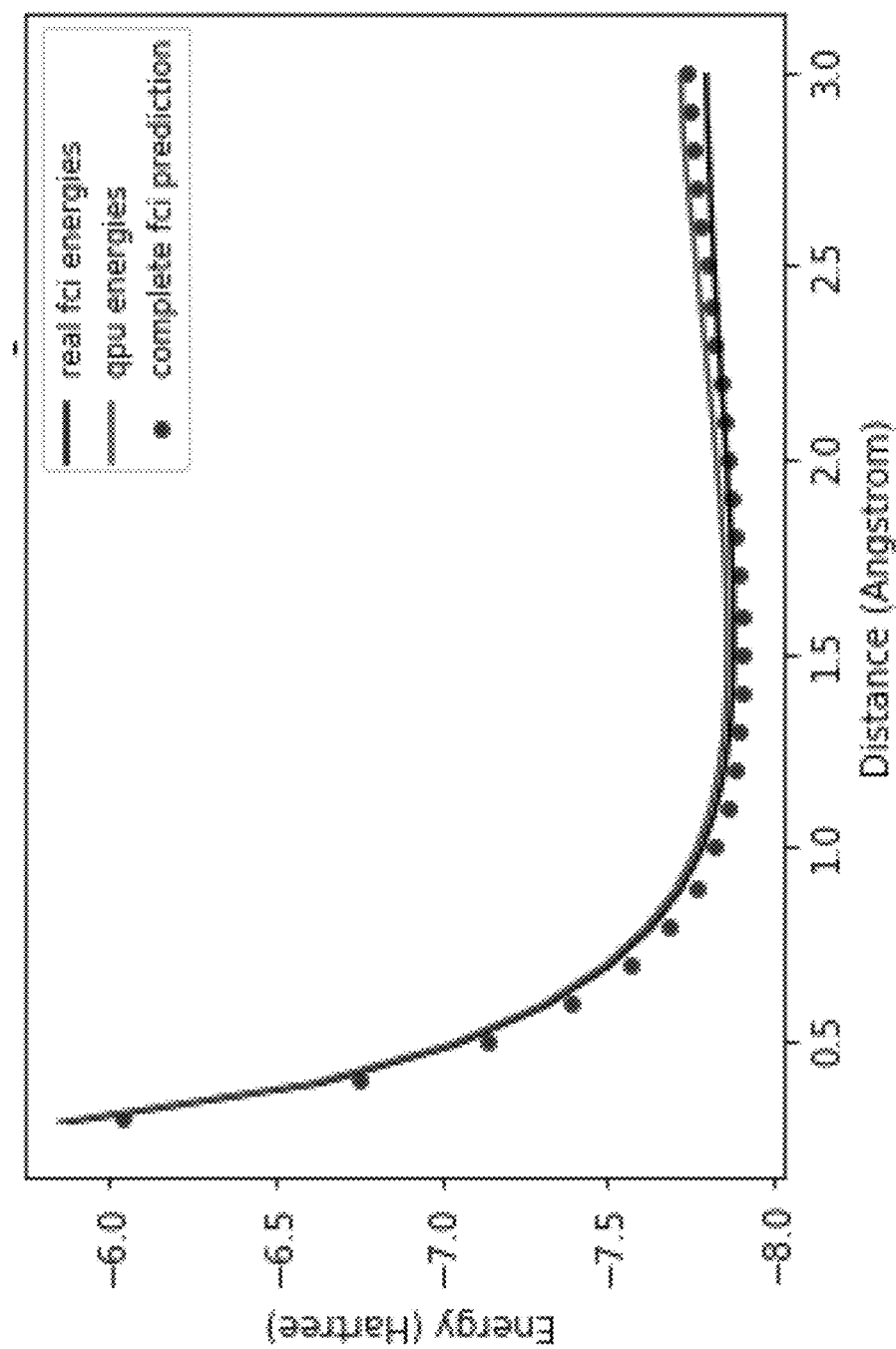
FIG. 3A illustrates example plots of predicted full configuration interaction (FCI) energies, classically determined real FCI energies, and quantum simulation energies.

The results described in FIG. 3A show that quantum simulation energies ("QPU energies") calculated from quantum simulation results generated by a QPU (e.g., a D-Wave system, etc.) acting as an optimal Ising (model) simulator slightly deviate from real FCI energies (e.g., classically computed with the Hartree method, etc.). The situation becomes even more apparent the more electrons a molecule has (e.g., 18 electrons, 12 electrons, etc.).

The quantum simulation energy curve ("QPU energies") calculated on the QPU may be compared with the classically calculated real FCI energy for simple molecules. As illustrated in FIG. 3A, the quantum simulation energy curve is very often in a shape similar to the shape of the real FCI energy curve, but is sometimes shifted along the y-axis (representing energy levels, etc.). In other cases (e.g., non-simple molecules, etc.), different shapes in quantum simulation energy curves and real FCI energy curves may or may not be observed. For simple quantum systems or molecules such as Lithium Hydride, it may be feasible to obtain the real FCI energy classically (e.g., with classical computation, etc.).

By training artificial neural networks (ANNs) on the atomic and molecular properties of small systems, the inaccuracies or differences of the quantum simulation energies in relation to the real FCI energies can be corrected. Additionally, the quantum simulation energy curve or the molecular energy curve of a molecule obtained with the QPU can be used to predict FCI energies with the ANNs based on the quantum simulation energies (e.g., "QPU energies" in FIG. 3C and FIG. 3D, etc.), bond lengths (e.g., "bond_lengths" in FIG. 3C and FIG. 3D, etc.), an atomic input vector (e.g., "hydrogen", "lithium", "oxygen", "beryllium", "phosphorus" and "nitrogen" in FIG. 3C and FIG. 3D, etc.), etc.

Molecular electronic information prediction techniques as described herein may be applied to molecules not represented in training data with which the ANNs are trained. While FIG. 3C describes applying these techniques to di-atomic molecules (e.g., "hydrogen"=1, "lithium"=1, "oxygen"=0, "beryllium"=0, "phosphorus"=0 and "nitrogen"=0 in FIG. 3C, etc.), the techniques may be generalized to n-atomic molecules (e.g., "hydrogen"=2, "lithium"=1, "oxygen"=1, "beryllium"=0, "phosphorus"=0 and "nitrogen"=0 in FIG. 3D, etc.) by adding respective bond lengths (e.g., between n atoms in the n-atomic molecules, etc.).

For example, the training data can be extended by molecules consisting of 3 atoms a, b, c, by adding two additional bond lengths: the bond lengths between a and b, a and c, and b and c. For di-atomic molecules, in the training data, these additional bond lengths can be set to a specific value or flag such as a constant (e.g., −1, an out-of-range value, a reserved value, etc.), which indicates there is no such interaction or no such bond in the di-atomic molecules.

Figure 4A:
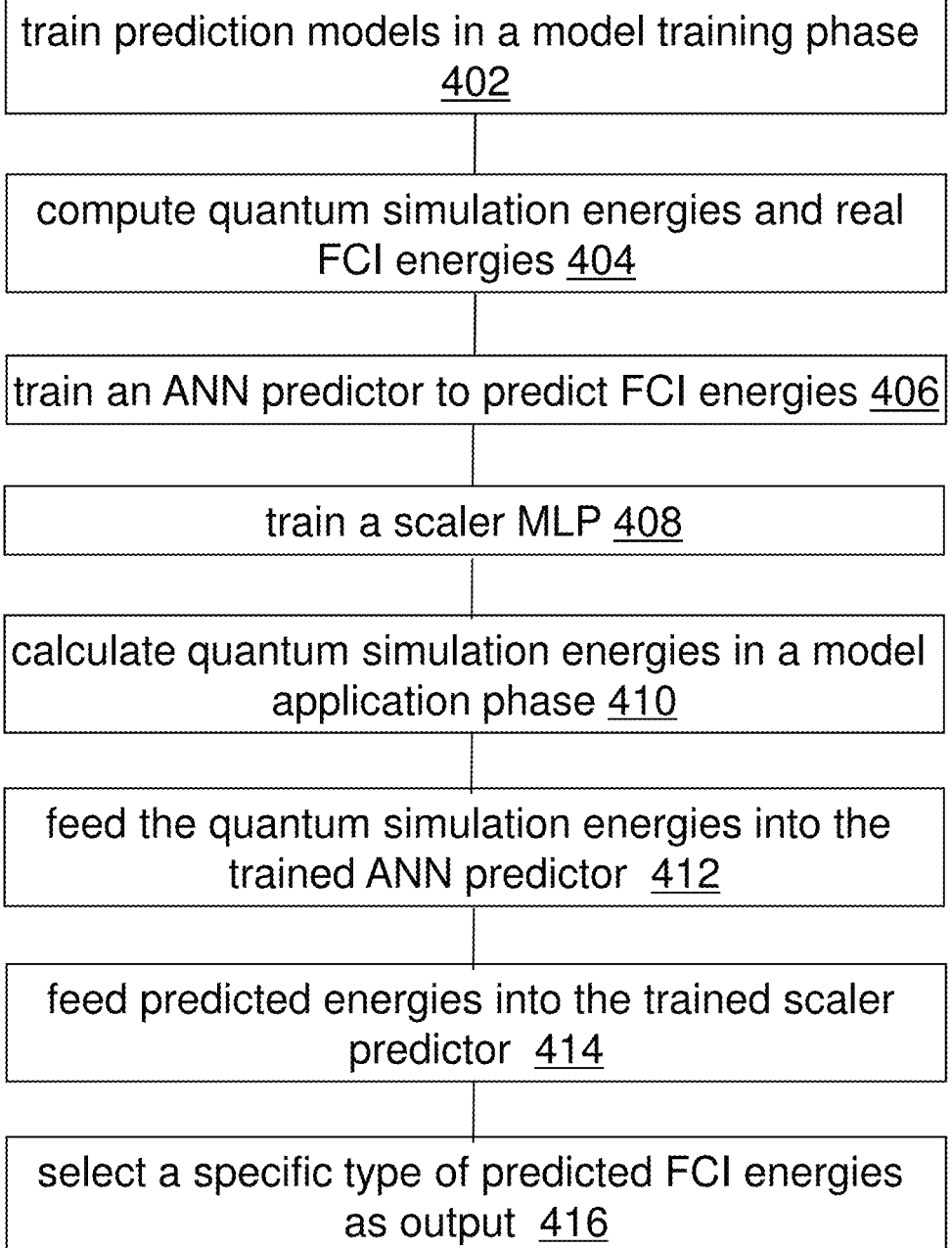

FIG. 4A illustrates an example flow 400 for training and applying prediction models for molecular electronic structural information, according to an embodiment. The various elements of flow 400 may be performed in a variety of systems (e.g., one or more classical computing devices, etc.), including systems such as system 100 described above. In an embodiment, each of the processes described below may be implemented using one or more computer programs, other software elements, and/or digital logic in any of a general-purpose computer or a special-purpose computer, while performing data retrieval, transformation, and storage operations that involve interacting with and transforming the physical state of memory of the computer. Flow 400 illustrates but one example flow for training and applying prediction models. Other flows may involve additional or fewer steps, in potentially varying arrangements.

Block 402 comprises training one or more prediction models (e.g., 108 of FIG. 1, 250 of FIG. 2B, etc.) in a model training phase. The model training phase may be partitioned into at least three component phases.

Block 404 comprises computing quantum simulation energies and real FCI energies (or classical FCI energies) of molecules (e.g., small molecules, simple molecules, etc.) for varying bond lengths using some or all techniques as described herein in the first component phase of the model training phase.

Figure 2B:
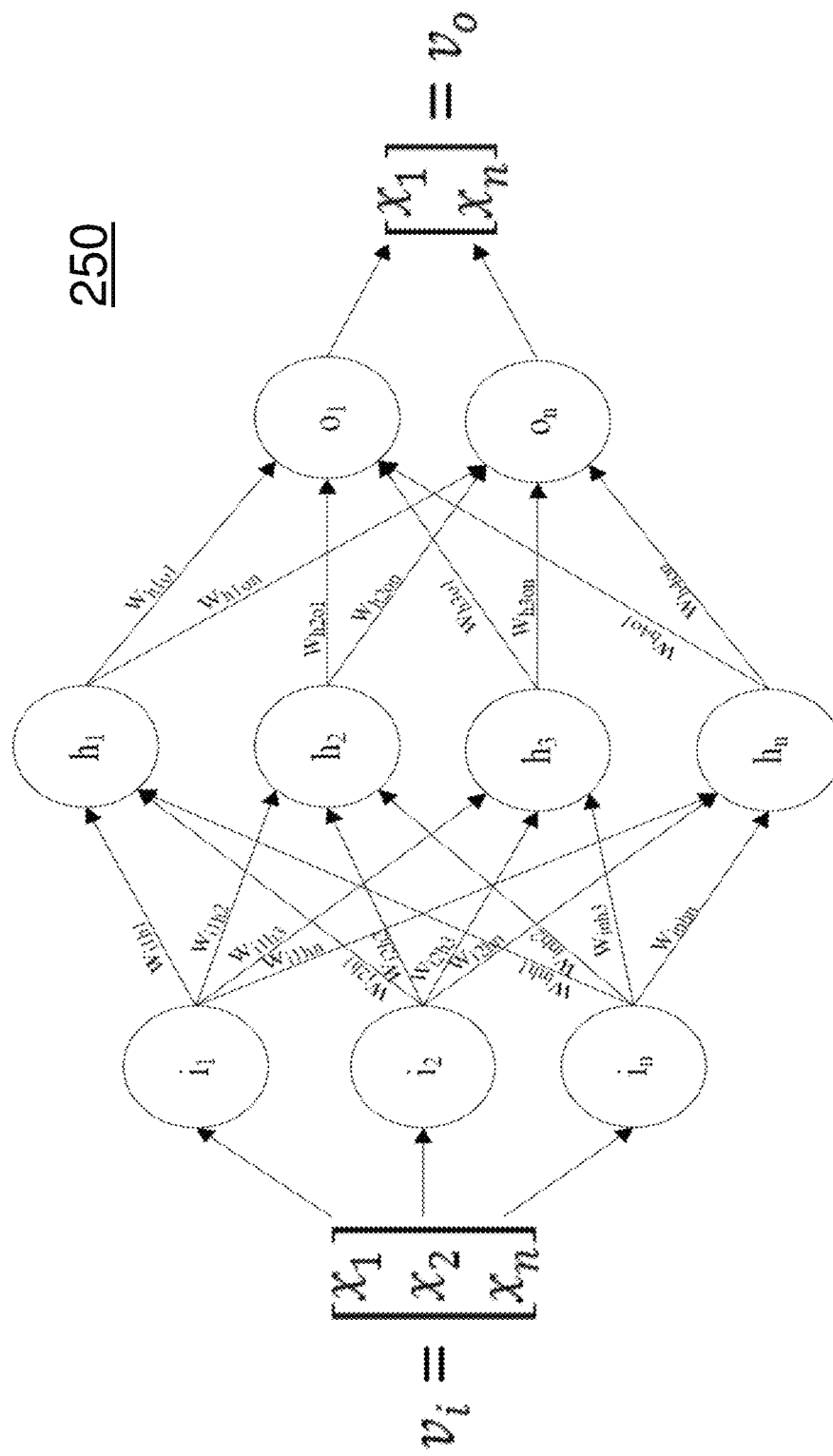
FIG. 2B illustrates an example ANN predictor representing a multi-layer perceptron.

Block 406 comprises training an ANN predictor (or a predictor implemented with an ANN) to predict FCI energies (e.g., classically calculated FCI energies, etc.) for varying bond lengths and different molecules. FIG. 2B illustrates an example ANN predictor representing a multilayer perceptron or MLP predictor 250.

Besides the quantum simulation energies ("QPU energies") for different bond lengths, an input vector (or instances thereof) to MLP predictor 250 may be used to distinguish whether (a kind of) an atom appears in a molecule and how many atoms (of the kind) appear in the molecule. As a result, MLP predictor 250 obtains or acquires the capability of turning atom-specific weights on and off, as well as learns the electronic influence one or many atoms of a kind have on others.

MLP predictor 250 can be trained on problem-specific molecules that are interesting for specific areas, for example on Li, O, H, Cu, Co for battery anodes, or even the whole periodic system. For the sake of simplicity, only a few atoms (e.g., six kinds of atoms, etc.) such as H, Li, O, Be, P, N may be included or represented in the training data. As illustrated in FIG. 3C and FIG. 3D, the first 6 values of the input vector following the bond length can be used to determine whether any of these atoms are present in a molecule.

These atoms used to compose the problem-specific molecules may be arranged in a sequence. A vector (e.g., during training, etc.) may comprise vector components formed with these atoms. For LiH, the vector may be set as 1, 1, 0, 0, 0, 0. For $H_2O$, the vector may be set as 2, 0, 1, 0, 0, 0. In the LiH example, there are one Hydrogen and one Lithium; thus the vector is set to 1 at positions 1 (H) and 2 (Li), as illustrated in FIG. 3C.

Additionally, various bond lengths and respective quantum simulation energies as determined with the QPU may be used as input to MLP predictor 250, as illustrated in FIG. 3D (as well as in FIG. 3C).

To determine the optimal structure of MLP predictor 250 (e.g., relatively simple predictor ANN, etc.), a (e.g., simple, etc.) search may be conducted through a hyperparameter-space comprising: activation functions (e.g., identity, logistic, tanh, relu, etc.); solvers (e.g., sgd, adam, lbfgs, etc.); alphas (e.g., 0.01, 0.02, 0.03, etc.); number of hidden layers (e.g., 1, 2, etc.); number of neurons per hidden layer (e.g., 1, . . . , 10, etc.); etc.

An activation function as described herein serves the purpose of scaling (the presented) output of a neuron layer into a proper range for further processing within an artificial neural network such as MLP predictor 250. The activation function is not restricted to specific function but rather can take any in a variety of forms. Common examples for activation functions may include the linear activation function with or without bias (equation or expression (10)), the logistic function (equation or expression (11)), the hyperbolic tangent (equation or expression (12)), or the rectifier linear unit (equation or expression (13)), as follows:

$$f(x) = x \tag{10}$$

$$f(x) = \frac{1}{1+e^{-x}} \tag{11}$$

$$f(x) = \frac{e^{2x}-1}{e^{2x}+1} \tag{12}$$

$$f(x) = \max(0, x) \tag{13}$$

Example solvers used to perform hyperparameter search with MLP predictor 250 include, but are not necessarily limited to only, any of: stochastic gradient descent, Adam, Limited Memory Broyden Fletcher Goldfarb, Shanno, and so forth. The search of alphas may be conducted with L2 penalty parameters (e.g., regularization term, etc.). Regularization in machine learning may be used to prevent overfitting, which would result in a prediction algorithm only being able to accurately predict what it has seen in the training data. A regularization term is added to prevent the prediction algorithm from fitting coefficients exactly in accordance with the training data. Example regularization parameters (or regularization terms) may include L2 regularization with the summed square of the weights and L1 regularization with the sum only, as respectively indicated in expressions (14) and (15), as follows:

$$w^* = \operatorname{argmin}_x \sum_j \left( t(x_j) - \sum_i w_i h_i(x_j) \right)^2 + \lambda \sum_{i=1}^k |w_i| \tag{14}$$

$$w^* = \operatorname{argmin}_x \sum_j \left( t(x_j) - \sum_i w_i h_i(x_j) \right)^2 + \lambda \sum_{i=1}^k w_i^2 \tag{15}$$

Additionally, the number of hidden layers and number of neurons per hidden layer may be searched through in the model training phase. In some operational scenarios, the architecture for MLP predictor 250 may be limited to two hidden layers and maximally 10 neurons per layer. An example tool such as "scikit-learn" may be used for implementing an MLP predictor as described herein.

Hyperparameters for the MLP predictor (or regressor) in an example implementation may include, but are not necessarily limited to only, some or all of: "batch_size" (e.g., auto, etc.); "learning_rate" (e.g., adaptive, etc.); "learning_rate_init" (e.g., 0.001, etc.); "power_t" (e.g., 0.5, etc.); "max_iter" (e.g., 1000, etc.); "shuffle" (e.g., True, etc.); "random_state" (e.g., 9, etc.); "tol" (e.g., 0.0001, etc.); "verbose" (e.g., False, etc.); "warm_start" (e.g., False, etc.); "momentum" (e.g., 0.9, etc.); "Nesterov's momentum" (e.g., True, etc.); "early_stopping" (e.g., False, etc.); "beta_1" (e.g., 0.9, etc.); "beta_2" (e.g., 0.999, etc.); "epsilon" (e.g., 1e_08, etc.); and so forth.

In the example implementation, the architecture or configuration of MLP predictor 250 converging best on the training data comprises nine (9) neurons in the first hidden layer, five (5) neurons in the second hidden layer, uses "lbfgs" as optimizer, "relu" as activation functions, L2-regularization set with a numeric value 0.03, etc.

MLPs as described herein finds or has application as function approximators. Two-layer perceptrons are capable of separating convex sets; any further layer enables MLPs to separate any sets. FIG. 2B describes an example MLP predictor 250 with three layers. MLP predictor 250 comprises three input neurons (e.g., $i_1$, $i_2$, $i_3$, etc.) presented with an input vector $v_i$ (e.g., $x_1$, $x_2$, $x_3$, etc.), four hidden neurons (e.g., $h_1$, $h_2$, $h_3$, $h_4$, etc.) and two output neurons (e.g., $o_1$, $o_2$, etc.) producing an output vector $v_i$ (e.g., $y_1$, $y_2$, etc.). The hidden neurons constitute an internal representation (or approximation) of the outside world, as transferred by the input neurons and adapted by input neurons, with corresponding weights. Every neuron of MLP predictor 250 makes use of an activation function. By way of illustration but not limitation, an example 3-layer MLP predictor with one output neuron may be give as follows:

$$x_t = h_2\left(w_0 + \sum_{j=1}^{i} w_j h_1\left(w_{0j} + \sum_{i=1}^{p} w_{ij} x_{t-i}\right)\right) + \epsilon_t \tag{16}$$

where the input layer has p inputs $x_{t-1}, \ldots x_{t-p}$; the hidden layer has l hidden nodes; the output layer has a single output $x_t$. These layers are fully connected by weights, where $w_{ij}$ represents a weight assigned to the i-th input for the j-th node in the hidden layer; $w_j$ represents a weight assigned to the output from the j-th node in the hidden layer; $w_j$ and $w_{0j}$ represent the biases; $h_1$ and $h_2$ represent activation functions; $\epsilon_t$ represents the uncertainty variable or white noise of MLP predictor (or ANN) 250.

The plain output of MLP predictor 250 without activation function and uncertainty variable may be specified or determined as follows:

$$o = \left(\sum_{i=1}^{n} \omega_i x_i + w_n\right) \tag{17}$$

where the input $x_i$ is multiplied with its corresponding weight coy and then summed up together with matrix columns' threshold $w_n$, in matrix examples represented by $(t_1, \ldots t_n)$, which may be further generalized with θ, as follows:

$$y = f\left(\sum_{i=1}^{n} w_i x_i + \theta\right) + \epsilon_t \tag{18}$$

where f denotes the activation function that is applied to the summed weights $\omega_i$ multiplied by the input values $x_i$, if the threshold is exceeded; Et represents the uncertainty variable or white noise. Additionally, expression (18) above takes into consideration a bias θ, which may or may not be used.

Block 408 comprises training a scaler MLP, which may implement an ANN-based prediction model, implemented as a second MLP predictor with different or additional input such as predicted energies from (a prior) MLP predictor 250, and so forth. The output of MLP predictor 250 may still not be accurate enough. The scaler MLP is trained on differences or errors (e.g., via back propagation, etc.) between predicted FCI energies from MLP predictor 250 and the real FCI energies (e.g., classically determined FCI energies, etc.). The scaler MLP receives the same input vector as MLP predictor 250 does as well as predictions generated by MLP predictor 250, uses the differences between predicted FCI energies from MLP predictor 250 and the real FCI energies as a target variable for minimization or optimization. The same or similar search may be conducted for the scaler MLP through the hyperparameter space as for MLP predictor 250. In an example implementation, the best architecture or configuration turns out to have nine (9) neurons in the first hidden layer, eight (8) neurons in the second hidden layer, hyperbolic tangent activation functions, "lbfgs" as optimizer, L2 regularization with a numeric value 0.03, and so forth.

3.5. Application Phase

Block 410 comprises calculating quantum simulation energies (or QPU energies as predicted by a quantum simulator) for molecules for varying bond lengths: Here, quantum simulation energies as generated through quantum simulation predict the energy surface of the molecules. These molecules may not have been seen by MLP predictor 250 and one or more scaler MLPs in the training data as described herein.

Block 412 comprises feeding the quantum simulation energies as predicted through quantum simulation (as input) into MLP predictor 250. FIG. 3A illustrates example plots (or functions) of FCI energies as predicted with MLP predictor 250, real FCI energies as classically determined by classical computers 106, and quantum simulation energies (or QPU energies) as generated through quantum simulation, for molecule LiH. As shown, the quantum simulation energies already provide very accurate prediction in relation to the real FCI for LiH. While MLP predictor 250 has not seen the molecule LiH in the training data, MLP predictor 250 further improves accuracies with its predicted FCI energies. The larger the bond length become, the more accurate the predicted FCI energies as generated by MLP predictor 250.

Figure 3B:
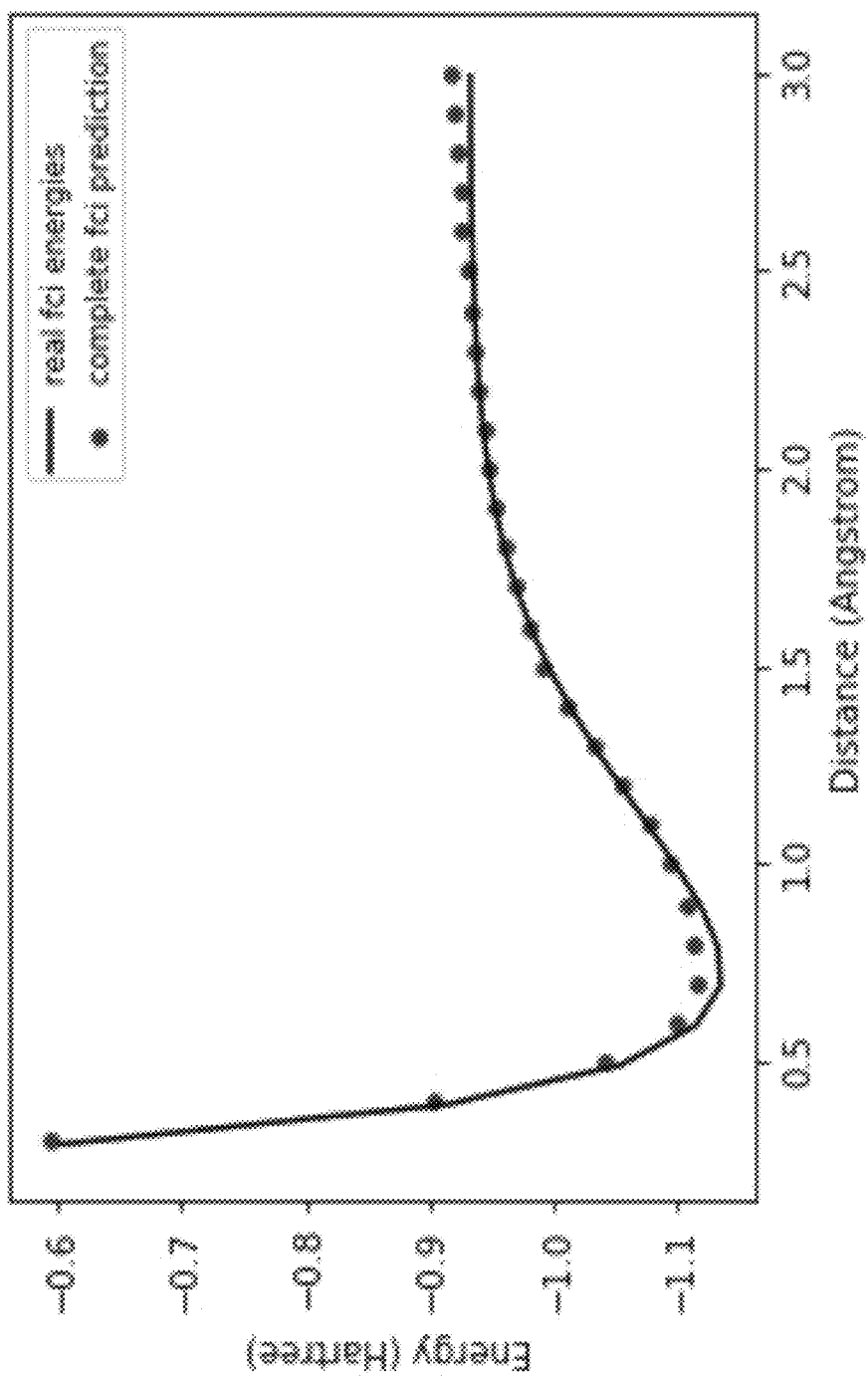
FIG. 3B illustrates example plots of predicted FCI energies and classically determined real FCI energies.

Block 414 comprises feeding predicted FCI energies into the scaler MLP. FIG. 3B illustrates example plots (or functions) of FCI energies as further predicted with the scaler predictor, and real FCI energies as classically determined by classical computers 106. By adding the output (or corrections) of the scaler MLP, the predicted FCI energies as further predicted with the scaler predictor becomes even closer (as compared with those generated by MLP predictor 250) to the real FCI energies as classically determined.

One or more types of predicted FCI energies may be generated: for example, predicted FCI energies generated by MLP predictor 250 alone; predicted FCI energies generated by a combination of MLP predictor 250 and the scaler predictor; predicted FCI energies generated by the scaler MLP. Different types of predicted FCI energies may diverge. There may be a variety of possible scenarios: the (plain) QPU prediction (or the quantum simulation energies) is the closest to the real FCI energies; the QPU energies as corrected by MLP predictor 250 and the scaler predictor is the closest to the real FCI energies; the QPU energies corrected by the scaler predictor alone is the closest to the real FCI energies; and so on.

Block 416 comprises selecting a specific type of predicted FCI energies as output, in operational scenarios in which multiple types of predicted FCI energies are generated.

By way of example but not limitation, the smoothness of predicted FCI energies may be used as a selection factor. The smoothness of a type of predicted FCI energies may be determined based at least in part on the standard deviation of a function representing the type of predicted FCI energies, as follows:

$$DIF_{ij} = x_i - x_j \quad (19)$$

$$S_X = \frac{\left(\sqrt{\frac{\sum_{i=1}^{N}(DIF_i - \overline{DIF})^2}{N-1}}\right)}{\overline{DIF}} \quad (20)$$

In some operational scenarios, the least smooth function among all functions representing all (candidate) types of predicted FCI energies may be deemed as the closest to the real FCI energy, and hence selected as output.

For the purpose of illustration only, it has been described that quantum simulation energies, predicted energies, etc., of molecule LiH may be generated using some or all techniques as described herein. It should be noted that, in various embodiments, quantum simulation energies, predicted energies, etc., of other molecules other than the molecule LiH, may be generated using some or all techniques.

Quantum simulation energies (or QPU energies) for molecules may be calculated for varying bond lengths. The quantum simulation energies may be used to predict the energy surface of molecules that prediction models as described herein have not seen in the training data used to train the prediction models. Quantum simulation energies predicting the energy surface of molecules may be fed as input into a predictor MLP. Predictions as described herein may also be fed as input into a scaler MLP. For example, the output of the scaler MLP may be added and post processing applied, which results in a prediction becoming even closer to real FCI energies (e.g., as illustrated in FIG. 3B).

4.0. EXAMPLE PROCESS FLOWS

FIG. 4B illustrates an example process flow according to an embodiment. In some embodiments, one or more computing devices or components may perform this process flow. In block 452, a system as described herein generates quantum simulation results for a molecule based on a quantum simulation of an electronic structure of the molecule. The quantum simulation of the electronic structure of the molecule is performed with one or more QPUs.

In block 454, the system creates an input vector comprising data field values derived from the quantum simulation results for the molecule, as generated based on the quantum simulation of electronic structure of the molecule.

In block 456, the system applies an electronic structural information prediction model to generate, based at least in part on the input vector, predicted electronic structural information for the molecule.

In an embodiment, the quantum simulation comprises: one or more of: molecular properties of the molecules, atomic properties of atoms present in the molecule, presence indications of atoms in the molecule, numbers of types of atoms present in the molecule, one or more bond lengths, quantum simulation energies, etc.

In an embodiment, a second electronic structural information prediction model is applied to generate, based at least in part on the quantum simulation results and the predicted electronic structural information generated by the electronic structural information prediction model for the molecule, second electronic structural information for the molecule.

In an embodiment, the electronic structural information prediction model is implemented with an artificial neural network representing a multi-layer perceptron.

In an embodiment, the electronic structural information prediction model is trained by training data in a model training phase; the training data is derived at least in part from quantum simulation results for one or more molecules based on quantum simulation of electronic structure of the one or more molecule; the training data is further derived at least in part from classically determined electronic structural information for the one or more molecules generated by one or more classical computers; differences derived from the quantum simulation results for the one or more molecules in the training data and the classically determined electronic structural information are used to optimize the electronic structural information prediction model.

In an embodiment, the predicted electronic structural information for the molecule at least includes predicted full configuration interaction energies for the molecule.

In an embodiment, the quantum simulation of electronic structure of the molecule is carried out with a quantum annealing process implemented by the one or more QPUs.

In an embodiment, a computing device is configured to perform any of the foregoing methods. In an embodiment, an apparatus comprises a processor and is configured to perform any of the foregoing methods. In an embodiment, a non-transitory computer readable storage medium, storing software instructions, which when executed by one or more processors cause performance of any of the foregoing methods.

In an embodiment, a computing device comprising one or more processors and one or more storage media storing a set of instructions which, when executed by the one or more processors, cause performance of any of the foregoing methods.

Other examples of these and other embodiments are found throughout this disclosure. Note that, although separate embodiments are discussed herein, any combination of embodiments and/or partial embodiments discussed herein may be combined to form further embodiments.

5.0. IMPLEMENTATION MECHANISM—HARDWARE OVERVIEW

According to one embodiment, the techniques described herein are implemented by one or more special-purpose computing devices. The special-purpose computing devices may be desktop computer systems, portable computer systems, handheld devices, smartphones, media devices, gaming consoles, networking devices, or any other device that incorporates hard-wired and/or program logic to implement the techniques. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques.

Figure 5:
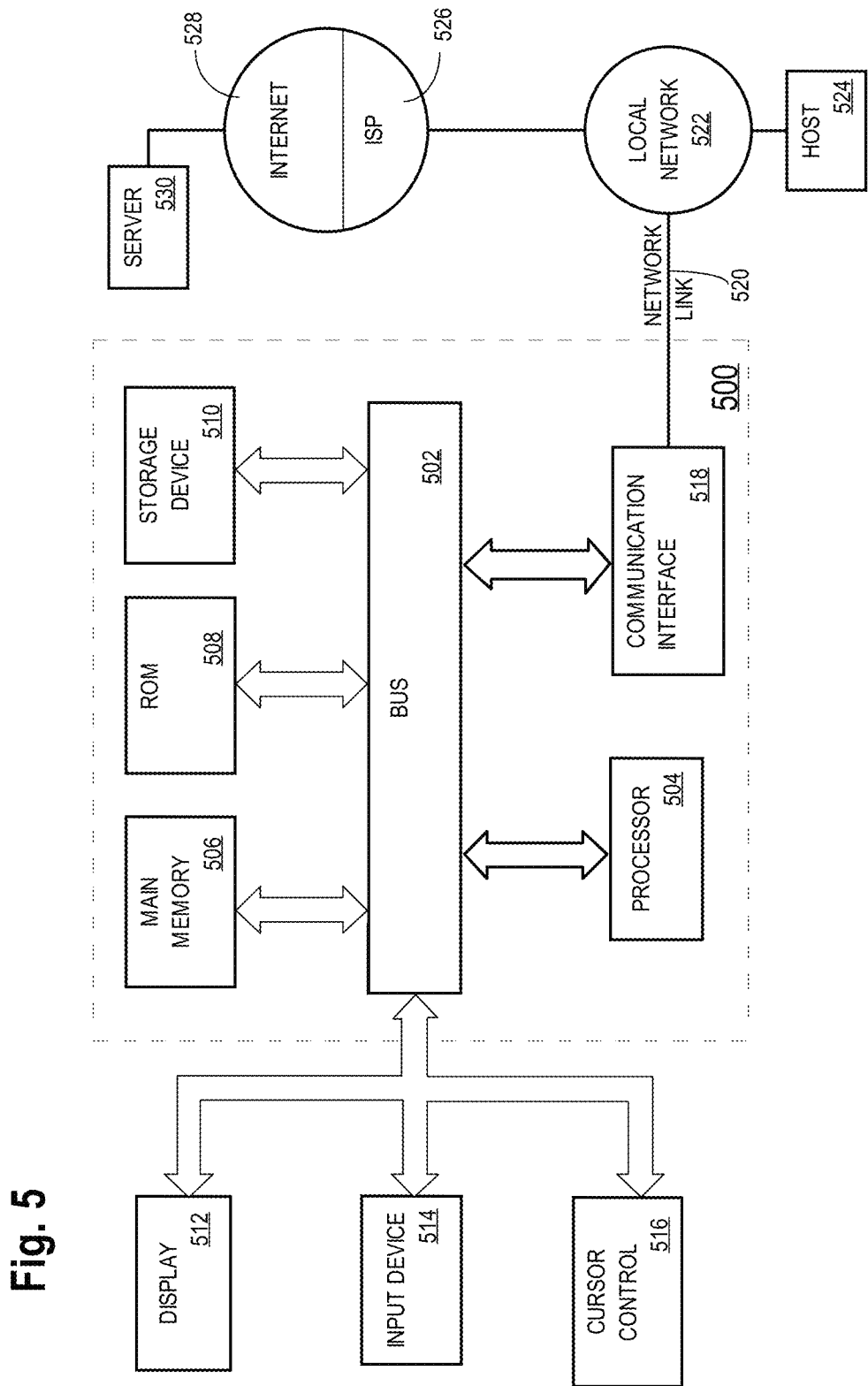
FIG. 5 is block diagram of a computer system upon which embodiments of the invention may be implemented.

FIG. 5 is a block diagram that illustrates a computer system 500 utilized in implementing the above-described techniques, according to an embodiment. Computer system 500 may be, for example, a desktop computing device, laptop computing device, tablet, smartphone, server appliance, computing main image, multimedia device, handheld device, networking apparatus, or any other suitable device.

Computer system 500 includes one or more busses 502 or other communication mechanism for communicating information, and one or more hardware processors 504 coupled with busses 502 for processing information. Hardware processors 504 may be, for example, a general purpose microprocessor. Busses 502 may include various internal and/or external components, including, without limitation, internal processor or memory busses, a Serial ATA bus, a PCI Express bus, a Universal Serial Bus, a HyperTransport bus, an Infiniband bus, and/or any other suitable wired or wireless communication channel.

Computer system 500 also includes a main memory 506, such as a random access memory (RAM) or other dynamic or volatile storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 into a special-purpose machine that is customized to perform the operations specified in the instructions.

Computer system 500 further includes one or more read only memories (ROM) 508 or other static storage devices coupled to bus 502 for storing static information and instructions for processor 504. One or more storage devices 510, such as a solid-state drive (SSD), magnetic disk, optical disk, or other suitable non-volatile storage device, is provided and coupled to bus 502 for storing information and instructions.

Computer system 500 may be coupled via bus 502 to one or more displays 512 for presenting information to a computer user. For instance, computer system 500 may be connected via an High-Definition Multimedia Interface (HDMI) cable or other suitable cabling to a Liquid Crystal Display (LCD) monitor, and/or via a wireless connection such as peer-to-peer Wi-Fi Direct connection to a Light-Emitting Diode (LED) television. Other examples of suitable types of displays 512 may include, without limitation, plasma display devices, projectors, cathode ray tube (CRT) monitors, electronic paper, virtual reality headsets, braille terminal, and/or any other suitable device for outputting information to a computer user. In an embodiment, any suitable type of output device, such as, for instance, an audio speaker or printer, may be utilized instead of a display 512.

In an embodiment, output to display 512 may be accelerated by one or more graphics processing unit (GPUs) in computer system 500. A GPU may be, for example, a highly parallelized, multi-core floating point processing unit highly optimized to perform computing operations related to the display of graphics data, 3D data, and/or multimedia. In addition to computing image and/or video data directly for output to display 512, a GPU may also be used to render imagery or other video data off-screen, and read that data back into a program for off-screen image processing with very high performance. Various other computing tasks may be off-loaded from the processor 504 to the GPU.

One or more input devices 514 are coupled to bus 502 for communicating information and command selections to processor 504. One example of an input device 514 is a keyboard, including alphanumeric and other keys. Another type of user input device 514 is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane. Yet other examples of suitable input devices 514 include a touch-screen panel affixed to a display 512, cameras, microphones, accelerometers, motion detectors, and/or other sensors. In an embodiment, a network-based input device 514 may be utilized. In such an embodiment, user input and/or other information or commands may be relayed via routers and/or switches on a Local Area Network (LAN) or other suitable shared network, or via a peer-to-peer network, from the input device 514 to a network link 520 on the computer system 500.

A computer system 500 may implement techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 510. Volatile media includes dynamic memory, such as main memory 506. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or solid state drive of a remote computer. The remote computer can load the instructions into its dynamic memory and use a modem to send the instructions over a network, such as a cable network or cellular network, as modulated signals. A modem local to computer system 500 can receive the data on the network and demodulate the signal to decode the transmitted instructions. Appropriate circuitry can then place the data on bus 502. Bus 502 carries the data to main memory 505, from which processor 504 retrieves and executes the instructions. The instructions received by main memory 506 may optionally be stored on storage device 510 either before or after execution by processor 504.

A computer system 500 may also include, in an embodiment, one or more communication interfaces 518 coupled to bus 502. A communication interface 518 provides a data communication coupling, typically two-way, to a network link 520 that is connected to a local network 522. For example, a communication interface 518 may be an integrated services digital network (ISDN) card, cable modem, satellite modem, or a modem to provide a data communication connection to a corresponding type of telephone line. As another example, the one or more communication interfaces 518 may include a local area network (LAN) card to provide a data communication connection to a compatible LAN. As yet another example, the one or more communication interfaces 518 may include a wireless network interface controller, such as a 802.11-based controller, Bluetooth controller, Long Term Evolution (LTE) modem, and/or other types of wireless interfaces. In any such implementation, communication interface 518 sends and receives electrical, electromagnetic, or optical signals that carry digital data streams representing various types of information.

Network link 520 typically provides data communication through one or more networks to other data devices. For example, network link 520 may provide a connection through local network 522 to a host computer 524 or to data equipment operated by a Service Provider 526. Service Provider 526, which may for example be an Internet Service Provider (ISP), in turn provides data communication services through a wide area network, such as the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

In an embodiment, computer system 500 can send messages and receive data, including program code and/or other types of instructions, through the network(s), network link 520, and communication interface 518. In the Internet example, a server 530 might transmit a requested code for an application program through Internet 528, ISP 526, local network 522 and communication interface 518. The received code may be executed by processor 504 as it is received, and/or stored in storage device 510, or other non-volatile storage for later execution. As another example, information received via a network link 520 may be interpreted and/or processed by a software component of the computer system 500, such as a web browser, application, or server, which in turn issues instructions based thereon to a processor 504, possibly via an operating system and/or other intermediate layers of software components.

In an embodiment, some or all of the systems described herein may be or comprise server computer systems, including one or more computer systems 500 that collectively implement various components of the system as a set of server-side processes. The server computer systems may include web server, application server, database server, and/or other conventional server components that certain above-described components utilize to provide the described functionality. The server computer systems may receive network-based communications comprising input data from any of a variety of sources, including without limitation user-operated client computing devices such as desktop computers, tablets, or smartphones, remote sensing devices, and/or other server computer systems.

In an embodiment, certain server components may be implemented in full or in part using "cloud"-based components that are coupled to the systems by one or more networks, such as the Internet. The cloud-based components may expose interfaces by which they provide processing, storage, software, and/or other resources to other components of the systems. In an embodiment, the cloud-based components may be implemented by third-party entities, on behalf of another entity for whom the components are deployed. In other embodiments, however, the described systems may be implemented entirely by computer systems owned and operated by a single entity.

In an embodiment, an apparatus comprises a processor and is configured to perform any of the foregoing methods. In an embodiment, a non-transitory computer readable storage medium, storing software instructions, which when executed by one or more processors cause performance of any of the foregoing methods.

6.0. EXTENSIONS AND ALTERNATIVES

As used herein, the terms "first," "second," "certain," and "particular" are used as naming conventions to distinguish queries, plans, representations, steps, objects, devices, or other items from each other, so that these items may be referenced after they have been introduced. Unless otherwise specified herein, the use of these terms does not imply an ordering, timing, or any other characteristic of the referenced items.

In the drawings, the various components are depicted as being communicatively coupled to various other components by arrows. These arrows illustrate only certain examples of information flows between the components. Neither the direction of the arrows nor the lack of arrow lines between certain components should be interpreted as indicating the existence or absence of communication between the certain components themselves. Indeed, each component may feature a suitable communication interface by which the component may become communicatively coupled to other components as needed to accomplish any of the functions described herein.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. In this regard, although specific claim dependencies are set out in the claims of this application, it is to be noted that the features of the dependent claims of this application may be combined as appropriate with the features of other dependent claims and with the features of the independent claims of this application, and not merely according to the specific dependencies recited in the set of claims. Moreover, although separate embodiments are discussed herein, any combination of embodiments and/or partial embodiments discussed herein may be combined to form further embodiments.

Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method for predicting electronic structural information of a molecule, the method comprising:
generating quantum simulation results for the molecule based on a quantum simulation of an electronic structure of the molecule, wherein the quantum simulation of the electronic structure of the molecule is performed with one or more quantum processing units (QPUs);
creating an input vector comprising data field values derived from the quantum simulation results for the molecule; and
applying an electronic structural information prediction model to generate, based at least in part on the input vector, predicted electronic structural information for the molecule, wherein the electronic structural information prediction model is trained with training data instances corresponding to other types of molecules than said molecule, wherein a training data instance in the training data instances includes (a) a second quantum simulation result of a second electronic structure of a second molecule generated with a quantum computer and (b) a classical computing result of the second electronic structure of the second molecule generated with a classic computer.

2. The method of claim 1, wherein the quantum simulation comprises: one or more of: molecular properties of the molecule, atomic properties of atoms present in the molecule, presence indications of atoms in the molecule, numbers of types of atoms present in the molecule, one or more bond lengths, and/or quantum simulation energies.

3. The method of claim 1, wherein a second electronic structural information prediction model is applied to generate, based at least in part on the quantum simulation results and the predicted electronic structural information generated by the electronic structural information prediction model for the molecule, second electronic structural information for the molecule.

4. The method of claim 1, wherein the electronic structural information prediction model is implemented with an artificial neural network representing a multi-layer perceptron.

5. The method of claim 1, wherein the electronic structural information prediction model is trained by training data in a model training phase; wherein the training data is derived at least in part from quantum simulation results for one or more molecules based on quantum simulation of electronic structure of the one or more molecules; wherein the training data is further derived at least in part from classically determined electronic structural information for the one or more molecules generated by one or more classical computers; wherein differences derived from the quantum simulation results for the one or more molecules in the training data and the classically determined electronic structural information are used to optimize the electronic structural information prediction model.

6. The method of claim 1, wherein the predicted electronic structural information for the molecule at least includes predicted full configuration interaction energies for the molecule.

7. The method of claim 1, wherein the quantum simulation of electronic structure of the molecule is carried out with a quantum annealing process implemented by the one or more QPUs.

8. One or more non-transitory computer readable media storing a program of instructions that is executable by a device to perform a method for predicting electronic structural information of a molecule, the method comprising:
generating quantum simulation results for the molecule based on a quantum simulation of an electronic structure of the molecule, wherein the quantum simulation of the electronic structure of the molecule is performed with one or more quantum processing units (QPUs);

creating an input vector comprising data field values derived from the quantum simulation results for the molecule; and applying an electronic structural information prediction model to generate, based at least in part on the input vector, predicted electronic structural information for the molecule, wherein the electronic structural information prediction model is trained with training data instances corresponding to other types of molecules than said molecule, wherein a training data instance in the training data instances includes (a) a second quantum simulation result of a second electronic structure of a second molecule generated with a quantum computer and (b) a classical computing result of the second electronic structure of the second molecule generated with a classic computer.

9. The media of claim 8, wherein the quantum simulation comprises: one or more of:
molecular properties of the molecule, atomic properties of atoms present in the molecule, presence indications of atoms in the molecule, numbers of types of atoms present in the molecule, one or more bond lengths, and/or quantum simulation energies.

10. The media of claim 8, wherein a second electronic structural information prediction model is applied to generate, based at least in part on the quantum simulation results and the predicted electronic structural information generated by the electronic structural information prediction model for the molecule, second electronic structural information for the molecule.

11. The media of claim 8, wherein the electronic structural information prediction model is implemented with an artificial neural network representing a multi-layer perceptron.

12. The media of claim 8, wherein the electronic structural information prediction model is trained by training data in a model training phase; wherein the training data is derived at least in part from quantum simulation results for one or more molecules based on quantum simulation of electronic structure of the one or more molecules; wherein the training data is further derived at least in part from classically determined electronic structural information for the one or more molecules generated by one or more classical computers; wherein differences derived from the quantum simulation results for the one or more molecules in the training data and the classically determined electronic structural information are used to optimize the electronic structural information prediction model.

13. The media of claim 8, wherein the predicted electronic structural information for the molecule at least includes predicted full configuration interaction energies for the molecule.

14. The media of claim 8, wherein the quantum simulation of electronic structure of the molecule is carried out with a quantum annealing process implemented by the one or more QPUs.

15. A system, comprising:
one or more computing processors;
one or more non-transitory computer readable media storing a program of instructions that is executable by the one or more computing processors to perform a method for predicting electronic structural information of a molecule, the method comprising:

generating quantum simulation results for the molecule based on a quantum simulation of an electronic structure of the molecule, wherein the quantum simulation of the electronic structure of the molecule is performed with one or more quantum processing units (QPUs);

creating an input vector comprising data field values derived from the quantum simulation results for the molecule; and applying an electronic structural information prediction model to generate, based at least in part on the input vector, predicted electronic structural information for the molecule, wherein the electronic structural information prediction model is trained with training data instances corresponding to other types of molecules than said molecule, wherein a training data instance in the training data instances includes (a) a second quantum simulation result of a second electronic structure of a second molecule generated with a quantum computer and (b) a classical computing result of the second electronic structure of the second molecule generated with a classic computer.

16. The system of claim 15, wherein the quantum simulation comprises: one or more of:
molecular properties of the molecule, atomic properties of atoms present in the molecule, presence indications of atoms in the molecule, numbers of types of atoms present in the molecule, one or more bond lengths, or quantum simulation energies.

17. The system of claim 15, wherein a second electronic structural information prediction model is applied to generate, based at least in part on the quantum simulation results and the predicted electronic structural information generated by the electronic structural information prediction model for the molecule, second electronic structural information for the molecule.

18. The system of claim 15, wherein the electronic structural information prediction model is implemented with an artificial neural network representing a multi-layer perceptron.

19. The system of claim 15, wherein the electronic structural information prediction model is trained by training data in a model training phase; wherein the training data is derived at least in part from quantum simulation results for one or more molecules based on quantum simulation of electronic structure of the one or more molecules; wherein the training data is further derived at least in part from classically determined electronic structural information for the one or more molecules generated by one or more classical computers; wherein differences derived from the quantum simulation results for the one or more molecules in the training data and the classically determined electronic structural information are used to optimize the electronic structural information prediction model.

20. The system of claim 15, wherein the predicted electronic structural information for the molecule at least includes predicted full configuration interaction energies for the molecule.

21. The system of claim 15, wherein the quantum simulation of electronic structure of the molecule is carried out with a quantum annealing process implemented by the one or more QPUs.

* * * * *